United States Patent [19]

Kumoi et al.

[11] Patent Number: 4,492,803
[45] Date of Patent: Jan. 8, 1985

[54] METHOD FOR PRODUCING BIS[β-(N,N-DIMETHYLAMINO)ALKYL]-ETHER

[75] Inventors: Sadakatsu Kumoi, Hikari; Keiji Mitarai, Shinnanyo; Yukihiro Tsutsumi, Tokuyama, all of Japan

[73] Assignee: Toyo Soda Manufacturing Co., Ltd., Shinnanyo, Japan

[21] Appl. No.: 536,028

[22] Filed: Sep. 26, 1983

[51] Int. Cl.³ .............................................. C07C 85/00
[52] U.S. Cl. ...................................................... 564/486
[58] Field of Search ......................................... 564/486

[56] References Cited

U.S. PATENT DOCUMENTS 2,501,556  3/1952  Whitman ........................ 564/486 X
3,400,157  9/1968  Poppelsdorf ...................... 564/486
3,428,685  2/1969  Hall ................................. 564/486 X
3,856,795  12/1974  Yardley ........................... 564/486 X

FOREIGN PATENT DOCUMENTS 48-7411  3/1973  Japan .................................. 564/486

Primary Examiner—Paul F. Shaver
Attorney, Agent, or Firm—Armstrong, Nikaido, Marmelstein & Kubovcik

[57] ABSTRACT

A method for preparing a bis[β-(N,N-dimethylamino)alkyl]ether by reacting a bismethohalide of bis[β-(N,N-dimethylamino)alkyl]ether represented by the following general formula

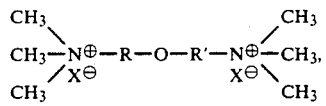

(wherein R and R' denote alkyl groups having 2-3 carbon atoms, and X denotes halogen atom,) with the aliphatic amine having 40°–170° C. of boiling point at atmospheric pressure and having one or two primary amino group in a molecule thereof at an increased pressure.

14 Claims, No Drawings

METHOD FOR PRODUCING BIS[β-(N,N-DIMETHYLAMINO)ALKYL]-ETHER

DETAILED DESCRIPTION OF THE INVENTION

The present invention relates to a method for producing a bis[β-(N,N-dimethylamino)alkyl] ether of the general formula given below:

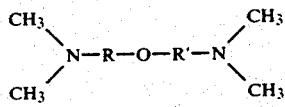

wherein R and R' represent alkyl groups having 2-3 carbon atoms.

The bis[β-(N,N-dimethylamino)alkyl] ether is known to be an industrially very useful compound as a catalyst for producing a polyurethane foam which accelerates reactions between an alcohol group and an isocyanate group and between a water and the isocyanate group.

There have been generally known the method of producing a tertiary amine compound by means of acting various nucleophilic reagents on the quaternary ammonium salt compound to effect a dealkylation reaction (14 III 1398 of New Experimental Chemistry Lecture, 1978) and also widely known the method of employing various amines having the active hydrogen as the dealkylation agent (395–407, 90 of Chem. Berichte—1957). Similarly, the method for producing the corresponding bis[β-(N,N-dimethylamino)alkyl]ether (hereinafter referred to etheramine) afforded by a demethylation reaction of a bismethohalide (hereinafter referred to bismethohalide substance) of the bis[β-(N,N-dimethylamino)alkyl]ether has been disclosed in U.S. Pat. No. 3,400,157 and Japanese Patent Publication No. Sho 48-7411 (U.S. Pat. No. 3,426,072).

In the U.S. Pat. No. 3,400,157, the dealkylation reaction of said bismethohalide is undergone in aqueous solution of the dimethylamine to obtain the corresponding ether amine at 67% of yield which is not a sufficiently high yield. In particular, in this process, it is necessary to separate and recover the unreacted dimethylamine (7.4° C. of boiling point) which have been excessively added to the reaction system, and the trimethylamine (2.9° C. of boiling point) of the reaction by-product respectively after the reaction is completed. The both amines has the very low boiling point and further the difference of these boiling points is small, and therefore the handling and the separating operation thereof are complicated. Furthermore, the handling of the methylamines having the ammonia-like smell on a large scale may cause the environmental pollution problem.

The Japanese Patent Publication No. Sho 48-7411 (U.S. Pat. No. 3,426,072) features in the manufacturing process of the etheramine the process of affording the demethylation reaction to said bismethohalide in the polyamines having high boiling point of not less than 220° C. and having a secondary or tertiary amino group together with a primary amino group of aminoethylethanolamine, triethylenetetramine, tetraethylenepentamine, pentaethylenehexamine, dipropylenetriamine and the like, under reduced pressure. In order to make these polyamines of the demethylation agent having the high boiling point applicable to an economically industrial process, the repetitive applications of the polyamines are required. However, the primary and secondary amino groups of the polyamines having the high boiling point are methylated due to said reaction, to decrease the amount of the active hydrogen of the amino groups and lower the capacity of the demethylation agent, and result in restricting the number of the re-application of the polyamines having the high boiling point greatly from aspect of the reaction.

The aminoethylethanolamine is poor in the amount of the active hydrogen per unit weight based on the amino groups. The ethyleneamines of the high boiling point such as the triethylene tetramine and the like contain a lot of secondary and tertiary amino groups and are relatively low in the content ratio of the primary amine group which has the maximum active hydrogen, an account of being a mixture of the compounds including the piperazine rings, and so they are also poor in the amount of the active hydrogen per unit weight. Accordingly, they can be said to be disadvantageous dealkylation agents from the economical aspect.

Furthermore, they have troublesome problems of the decomposition of the polyamines themselves, accompanies with drop of the recovery yield of the polyamines after the reaction and drop of the content ratio of the amino groups in the polyamines.

The reaction yield of said etheramine is also 70–71% which are not so improved in comparison with the case of the dimethylamine.

In the process of producing the etheramine said bismethohalide of the raw-material and the amines of the demethylation agent are relatively expensive, and therefore it is desired to be able to produce said etheramine at higher yield. Still more, the amines of the demethylation agent suffers the structural changes such as methylation and the like from the reaction concerned, to be limited in the repetitive applications thereof. Thus, the demethylation agents, which have excellent capacity in the production amount of said etheramine per unit weight of the amine and are economically advantageous, have been expected.

In the light of the above circumstances, the inventors of this invention have made researches in the problem with their earnest efforts and found that the etheramine had been able to be produced at a marvelous high yield by reacting the bismethohalide with the aliphatic monoamine or diamine compound having the primary amino group only as an amino group as the demethylation agent under increased pressure, so they have completed this invention.

Namely, this invention proposes a method for producing a bis[β-(N,N-dimethylamino)alkyl]ether by reacting a bismethohalide of a bis[β-(N,N-dimethylamino)alkyl]ether represented by the general formula:

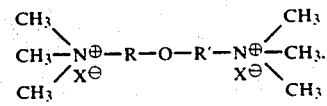

(wherein R and R' represent alkyl group containing 2-3 carbon atoms and X represents halogen atom.) with an aliphatic amine having 40°-170° C. of boiling point under atmospheric pressure and having 1-2 primary amino groups in the molecule thereof, under increased pressure..

The bismethohalide of the raw material used in this invention is represented by the following general formula:

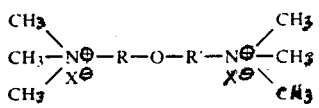

Namely, the bismethohalide of the bis[β-(N,N-dimethylamino)alkyl]ether wherein, in general, R and R' represent alkyl groups containing 2-3 carbon atoms and X represents halogen atom can be widely used as the raw material therefor. Among the bismethohalide, from economical stand points and procurement circumstances of the raw material, as the preferable raw materials used in this invention are exemplified bismethochloride of bis[β-(N,N-dimethylamino)ethyl]ether, bismethochloride of [1-methyl-2(N,N-dimethylamino)ethyl-2'(N,N-dimethylamino)ethyl]ether and bismethochloride of bis[1-methyl-2(N,N-dimethylamino)ethyl]-ether.

The aliphatic amine used in this invention is the compound having a boiling point in range of 40°-170° C. under atmospheric pressure and having 1-2 primary amino groups in the molecule thereof. In other words, the aliphatic amine is featured in not containing the secondary or tertiary amino group but having the primary amino group only in the molecule thereof.

The general chemical formula of the aliphatic amines is represented as follows.

$NH_2$—R wherein R represents alkyl group containing not less than 4 carbon atoms.

$NH_2$—R''—$NH_2$ wherein R'' represents alkylene group containing not less than 2 carbon atoms.

As the typical compounds thereof, butylamine, ethylenediamine, propanediamine, butanediamine and the like are exemplified. Among these amine compounds, ethylenediamine, 1,2-propanediamine, 1,3-propanediamine and 1,4-butanediamine are preferably used from the aspects of reactive activity, yield and economy. In particular, the ethylenediamine and the propane diamine are excellent in the production capacity of the etheramine per unit weight of amine and very advantageous economically.

The aliphatic primary amine compounds of not more than 40° C. boiling point may be used for the reaction but the use of these amines of the low boiling point requires the complicated recovery operations as in the case of dimethylamine and further requires the operation under a relatively high reaction pressure, so the use thereof is not preferable from the aspect of the apparatus. On the other hand, the aliphatic primary amine compounds of not less than 170° C. of boiling point may be also used for the reaction but are not preferable from the operative and economical aspects since there arise troublesome problems in separating these amines of high boiling point from said etheramine by distillation and the production capacity of the etheramine per unit weight of amine is low.

The method of the reaction in this invention essentially comprises the processes that the bismethohalide of the raw material and the aliphatic primary amine based on this invention are firstly charged into the reactor and then are subjected to a reaction at an elevated temperature to produce the etheramine of the object. The addition amount of the aliphatic primary amine is usually more than 2 mols to 1 mol of said bismethohalide. For example, in case of performing the reaction in a non-aqueous system, the aliphatic primary amine should be added by at least 2 mols, preferably not less than 3 mols, in order to disperse said bismethohalide. The addition of less than 2 mols aliphatic primary amines do not improve the dispensibility and the drop of the yield appears. The upper limit for the addition amount of the aliphatic primary amine is not particularly specified but selected for an efficient amount in consideration of the production efficiency of the reactor and the recovery amount of amines after the reaction thereof, etc.

The reaction is usually undergone without solvent and diluent but may be undergone under the existence of water and various organic diluents. In case the aqueous solution of the bismethohalide is used as the raw material, the reaction has an advantageous on the operation aspect since the reaction becomes a liquid phase reaction by using water as the solvent but the use of water is not advantageous since phenomenon such as accelerating of corrosion in the reactor becomes remarkable under the co-existence of water. These diluents are effective to advance the dispersibility of the bismethohalide but the addition amount of those diluents are usually less than the equal weight parts to said bismethohalide.

The reaction of this invention is usually performed under the temperature of 140°-190° C. The temperature of not less than 190° C. makes the control of the reaction temperature resulted by a quick reaction difficult and brings about drop of yield due to the decomposition of the product. Further, the temperature of not more than 140° C. is not practicable because of a slow reaction rate.

The reaction between the bismethohalide and the aliphatic amine requires the sufficient contact between them over the period up to completion of the reaction and it is indispensable to perform it under increased pressure to prevent the aliphatic amine from distilling out towards the outside of the reaction system during the reaction. The reaction pressure varies, depending on the kind and amount of the aliphatic amine and the diluent, and on the reaction temperature, but this reaction can be usually performed under a relatively low pressure of lower than 10 kg/cm².

For the industrial production of said etheramine, the aliphatic amine is required to be used repeatedly for the reaction to advance economical value of the process. Namely, after the reaction, the reaction mixture comprising hydrochloride salts of amines are added with alkaline compound to liberate and recover the amines. The alkaline compounds used for the neutralization are not specified but exemplify hydroxide, carbonate, etc. of the alkali metal. The sodium hydroxide or potassium hydroxide is usually used as an aqueous solution and the addition amount thereof is not less than twice mol equivalents of the bismethohalide of the raw material, e.g. approximately 2.0-2.2 times mol equivalents. After the neutralization, the aliphatic amine and said etheramine are recovered from the mixture consisted of the amines, water and salt through the conventional separating means of distillation, filtration, extraction, etc. The recovered aliphatic amines are reused for the subsequent reactions repeatedly. The repetitive applications of the aliphatic amines as the demethylation agent increase the production amount of said etheramine per unit weight of amine, thereby remarkably elevating economical value of the process.

As in the foregoing description, the application of the aliphatic amine as the demethylation agent can obtain the etheramine yield of exceeding the conventional reaction yield greatly and still maintains a very high yield of said etheramine and hardly result drop of the demethylation capacity even if it is used three times repeatedly. The aliphatic amine of this invention differs from the polyamines of high boiling point containing many secondary or tertiary amine groups and is not so much recognized of the phenomenon for the decomposition of the amine itself e.g. drop of reaction activity due to the elimination of the amino group, etc. Therefore, the aliphatic primary amine proposed by this invention is recognized as a very advantageous demethylation agent in the industrial process which is suitable for the repetitive reactions.

This invention proposes one improved method of the aforesaid basic invention relating to producing bis[β-(N,N-dimethylamino)alkyl]ether.

In the basic invention, the method for recovering the beforementioned aliphatic amine comprises multistage separation such as distillation-centrifugal separation-distillation of the reaction mixture after neutralized, and therefore it constitutes a complicated separating and recovering method. Additionally, there is another complication of handling a solid-containing slurry, and therefore it can not be necessarily said to be a favorable process from the aspect of operating property.

In case the employed aliphatic amine forms no azeotrapic mixture with water, it is possible to recover said aliphatic amine by removing water selectively from the reaction mixture after neutralized through distillation, followed by further desalting and distillation. However, in case of using the aliphatic amine which forms an azeotrapic mixture with water such as ethylene diamine as the demethylation agent, water can not be selectively removed through conventional distillation under ordinary pressure. In other words, as to some kinds of the aliphatic amines, it is difficult to separate and recover the aliphatic amine from water and salt through the abovestated process comprising a series of operations such as dehydration by distillation-desalting by centrifugal separation-distillation.

In the production process of etheramine in which the raw material bismethohalide is reacted with the aliphatic amine having 40°-170° C. boiling point and having primary amine and further the aliphatic amine recovered from the reaction mixture is used repeatedly, there has been strongly desired a very simple way of separating and recovering the aliphatic amine which can be applied universally without depending on the kind of the aliphatic amine and in even case of employing said aliphatic amine of any chemical structure as the demethylation agent.

In particular, there has been strongly desired the establishment of the industrial production process of etheramine in which the separating and recovering process is simple and excellent in the operating property and no special separating apparatus is required, thereby being advantageous in the aspect of facilities and being economically excellent. The inventors, upon reviewing these circumstances, has elaborately studied to find out a new fact that a reaction of the bismethohalide with the aliphatic amine having primary or secondary amino group yields the reaction mixture which is separated into two of an upper layer, and a lower layer, etheramine of the objected product can be recovered from the upper layer and the aliphatic amine of the demethylation can be recovered from the lower layer.

Furthermore, they had found that the recovered aliphatic amine can be reused as such for the reaction with the bismethohalide, if it is treated with addition of alkali metal hydroxide when the aliphatic amine is recovered from the lower layer, and have completed this improved invention, based on this finding.

That is, this invention also propose a method for producing a bis[β-(N,N-dimethylamino)ethyl]ether wherein a bismethohalide of bis[β-(N,N-dimethylamino)ethyl]ether represented by a general formula

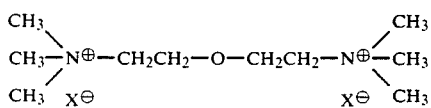

(X denotes halogen atom)

is reacted with the aliphatic amine, which comprises (a) separating and recovering respectively an upper layer liquid and a lower layer liquid from a reaction mixture having two separated upper and lower layers obtained by the reaction of said bismethohalide with the aliphatic amine having primary or secondary amino group (b) adding alkali metal hydroxide to the lower layer liquid so as to be in a concentration of 10-55 weight% to water amount of the lower layer liquid and thereafter recovering the aliphatic amine (c) further reusing the recovered aliphatic amines for the reaction with said bismethohalide compound.

In case of this improved method, the aliphatic amine which can be used in this invention is not particularly restricted, so long as it contains primary or secondary amino group in the molecule thereof. However, among these the aliphatic amines having the active hydrogen which comes from the amino group, a compound having the boiling point in range of 40°-170° C. under atmospheric pressure and having 1-2 primary amino groups in the molecule thereof is the very useful aliphatic amine from the aspects of the reaction yield and the economics, for it can produce etheramine at high yield. Exemplifying the typical compounds thereof, n-propylamine, butylamine, ethylenediamine, propanediamine, butanediamine and the like are preferable used. Particularly, ethylenediamine and propanediamine are used as very useful aliphatic amines, for they are excellent in the production capacity of etheramine per unit weight of the amine, moreover these are easily available and so on.

The production process of etheramine in this invention essentially comprises a step of reacting the raw material bismethohalide with the aliphatic amine of demethylation agent and a step of separating and recovering the aliphatic amine from the reaction mixture in order to reuse it as the demethylation agent.

The mode of reaction in the above steps is not particularly restricted, but it is usually performed in the following way.

That is, the reaction of the bismethohalide with the aliphatic amine is practiced under ordinary pressure or increased pressure at a temperature of 100°-190° C. In case the aliphatic amine of relatively low boiling point is employed, the reaction is carried out under increased pressure at an elevated temperature, in order to prevent the aliphatic amine from escaping outside the reaction system. Also, in case an aliphatic amino having a relatively high boiling point is employed, the reaction may be carried out under ordinary pressure with refluxing and cooling.

The addition amount of the aliphatic amine is usually not less than 2 mols to 1 mol of the bismethohalide. The upper limit of the addition amount of the aliphatic amine is not particularly restricted, but an effective amount thereof is selected in consideration of the production efficiency of the reactor, the recovering charge and the like accompanied with the recovered amount of the aliphatic amine after used.

The aliphatic amine not only acts as demethylation agent of the bismethohalide but also has a function of diluting and dispersing agent in order to improve the dispersing property of the bismethohalide.

Therefore, it is not always necessary to add the diluting and dispersing agent into the reaction system additionally.

As described in Japanese patent publication No. Sho 48-7411 (U.S. Pat. No. 3,426,072), it is generally practiced in a system of using an aliphatic amine which is close to nonaqueous system as the diluting and dispersing agent or in a system in which a diluent of glycolethers is added.

As water is used in the process of producing the raw material bismethohalide, the water accompanied with the raw material is introduced into the reaction system of the present process. As this result, the reaction can be performed in a system of adopting water as the diluent together with the aliphatic amine likewise as the reaction method of this invention.

The use of the diluent such as water and the like is not particularly advantageous in the aspects of the etheramine yield and the efficiency of the reactor, so the addition amount thereof is favourably not more than equal weight parts to the bismethohalide.

In order to produce etheramine on industrial scale, it is important to elevate the economical value of this process by recovering the aliphatic amine from the reaction mixture obtained by the aforesaid reaction, followed by reusing it repeatedly.

In any reaction method of the reaction of the bismethohalide aqueous solution with the aliphatic amine and of the reaction of the solid bismethohalide with the aliphatic amine, the reaction mixture after completion of the reaction come to be separated into two of the upper and lower layers. The separating and recovering method of this invention consists of separating and recovering the upper layer liquid and the lower layer liquid from the reaction mixture separated into two layers, followed by performing the following treatment.

That is, the upper layer liquid consisting of mainly etheramine undergoes distillation as such to give the product of etheramine. At this time, the part of aliphatic amine dissolved into etheramine layer is also recovered, so the recovered one can be repeatedly reused as the demethylation agent.

On the other hand, the almost part of aliphatic amine exists in the lower layer liquid in state of being free and in state of hydrogen halide acid salt. With addition of alkali metal hydroxide to this lower layer liquid, neutralization reaction occurs at first, and the free amine comes to be formed. After neutralization of hydrogen halide acid, alkali metal hydroxide is added thereto so that the concentration of alkali metal hydroxide may be 10-55 weight%, preferably 20-52 weight% to water content in the liquid.

The liquid treated like this comes to separate into a slurry-like lower layer containing deposited solid of neutral salts etc. and a supernatant liquid of liberated amines. This liquid phase containing amines is separated and recovered from the slurry-like solid phase to obtain the recovered amine.

Furthermore, said recovered aliphatic amines contain various amines produced by side reactions and small amount of inorganic compounds etc., but the recovered aliphatic amines can be reused as it is in the reaction with the bismethohalide. The alkali metal hydroxide used in this invention is not particularly restructed, but sodium hydroxide or potassium hydroxide is usually in state of solid or aqueous solution.

In order to depress the water amount brought into the system to the utmost, it is recommendable to use solid alkali metal hydroxide.

The concentration of alkali metal hydroxide added further after the neutralization is defined as follows.

$$\text{The concentration of alkali metal hydroxide} = \frac{C}{A + B + C} \times 100\%$$

A: weight of water in the lower layer liquid after the reaction of producing etheramine B: weight of water formed by the neutralization reaction C: weight of alkali metal hydroxide existing in the system When the concentration of alkali metal hydroxide in the system is less than 10 weight%, neutral salts are still dissolved in the recovered aliphatic amine liquid, so desalting from the recovered aliphatic amine layer is not enough. Then, in case the liquid mixture of aliphatic amines recovered under these condition is used as it is repeatedly as the demethylation agent, yield of etheramine is lowered and therefore it is not favourable as the demethylation agent. Even if alkali metal hydroxide is added so as to be a concentration of more than 55 weight%, the recovered aliphatic amine is not endowed with more favourable property as the demethylation agent, and then it brings about only economical loss due to excess addition of alkali metal hydroxide. The operating conditions at the time of adding alkali metal hydroxide to the lower layer liquid and treating it with stirring are not particularly restricted, but the following conditions are preferably selected.

That is, the treatment is operated at a temperature of more than 20° C. but lower than boiling point of the aliphatic amine, preferably at a temperature of 40°-120° C. Higher the treatment temperature is, sooner the treatment operation is completed, and effective treatment of the lower layer liquid becomes feasible.

In case the treatment is performed in a temperature range of 40°-120° C., the treatment is usually completed within 0.5-5 hours, so the slurry-like solid containing neutral salts etc. come to be sedimented. When, after leaving it to stand, the supernatant liquid is separated and recovered from the slurry-like solid phase, amines existing in the lower layer can be almost quantatively recovered. Also, the separation of solid phase and liquid phase may be practiced by centrifugal separation.

Even if the liquid recovered by only thus phase-separating operation is repeatedly used as the demethylation agent, furthermore can be still produced at high yield.

As beforementioned, the recovered aliphatic amines can be repeatedly used as the demethylation agent by a very simple separating operation comprising the combination of alkali metal hydroxide treatment of etheramine resulting reaction mixture with phase-separating operation.

The production process of etheramine by this invention not only is improved remarkably in operations but also requires no special facilities. That is, the industrial production of etheramine becomes feasible by utility instruments, and therefore it can be said to be a very useful method from the aspect of facilities. Furthermore, even if the aliphatic amines recovered by the method based on this invention are used repeatedly for the reaction with the bismethohalide, etheramine can be constantly produced at high yield.

In other words, the method of this invention can be said to be an industrial process for producing bis[β-(N,N -dimethylamino)ethyl]ether which is extremely excellent by economical reasons also.

This invention further proposes another improved method of the aforesaid basic invention. In the basic invention, the method for recovering the beforementioned aliphatic amine comprises multistage separation operations such as distillation of the reaction mixture after neutralized-centrifugal separation-distillation, and therefore it constitutes a very complicated separating and recovering method.

An important point in the process of recovering the aliphatic amine of the demethylation agent for recycled use thereof lies in that the salt generated by neutralization, water carried into the reaction system accompanied with the raw material bismethohalide and the recovered aliphatic amine, further water generated by the neutralization reaction and other substances which give unfavorable influences on the etheramine yield are removed out of the system with good efficiency through a simple operation.

Upon reviewing these circumstances, the inventors had made elaborate studies to find out the following new facts.

(1) An extremely simplified treating method of the reaction mixture capable of performing neutralization, desalting and dehydration of the reaction mixture rapidly all at once by practicing an essentially simple operation consisting of adding alkali metal hydroxide to the reaction mixture of the bismethohalide substance with the aliphatic amine having active hydrogen based on amino group (2) Etheramine can be produced at high yield in even case the liquid treated by the above method is subjected to crude distillation to separate and recover a distillate of boiling point of less than 170° C. comprising mainly said aliphatic amines and various kind of organic matters, thereafter the recovered one is re-used repeatedly as the demethylation agent.

This improved invention has been completed, based on the findings of the above new facts (1) and (2).

This invention further also proposes a method for producing a bis[β-(N,N-dimethylamino)ethyl]ether wherein a bismethohalide compound of bis[β-(N,N-dimethylamino)ethyl]ether represented by a general formula

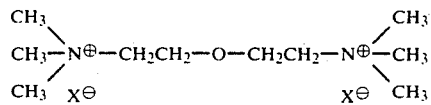

(X denotes halogen atom)

is reacted with an aliphatic amine having boiling point of 40°-170° C. under atmospheric pressure and having 1-2 primary amine group in the molecule thereof, which comprises (a) adding alkali metal hydroxide so as to be 10-55 weight% to water amount in the reaction system, after completion of the reaction of said bismethohalide with said aliphatic amine (b) separating and recovering a liquid phase consisted of the amines (c) separating the recovered amine into a distillate of boiling point of not exceeding 170° C. under atmospheric pressure and a distillate of that of exceeding 170° C. by distillation (d) reusing the recovered amine having boiling point of not exceeding 170° C. under atmospheric pressure in the reaction with said bismethohalide. In case of this improved method, the aliphatic amine which can be used in this invention is one having boiling point of 40°-170° C. and having 1-2 primary amino groups in the molecule thereof.

The separating and recovering method of this invention consists of performing the following treatments.

That is, the reaction mixture of the raw material bismethohalide with the aliphatic amine is consisted of the resultant etheramine, the mixture of said aliphatic amines which has received methyl group from the bismethohalide to be partially denatured in the structure thereof, water which has been brought into the reaction system with the raw material, hydrogen halide acid and various side reaction products.

With addition of alkali hydroxide to this reaction mixture, at first hydrogen halide acid is neutralized to produce liberated amines, and then alkali metal hydroxide is added thereto so that the concentration of alkali metal hydroxide may be 10-55 weight%, preferably 20-52 weight% to water content in the liquid. The liquid treated like this comes to separate into a slurry-like solid phase and a liquid phase consisting of mainly various amines. From the solid and liquid phase obtained like this, the liquid phase consisting of amines is separated and recovered. Further, the recovered amines are separated into a distillate of boiling point of not exceeding 170° C. (under atmospheric pressure) and etheramine of a distillate of one of exceeding 170° C. Etheramine is available as the product, and the recovered amines of boiling point of not exceeding 170° C. which consist of mainly the mixture of said aliphatic amines can be reused as it is, without doing rectification, in the reaction with the bismethohalide.

The alkali metal hydroxide of this invention is used likewise as in the foregoing improved invention, in respect to the kind, the mode of addition, the concentration thereof further added after the neutralization and so on.

When the concentration of alkali metal hydroxide in the system undergoing further addition thereof after the neutralization is less than 10 weight%, dehydration from the reaction mixture is not enough. Hence, if the distillate of boiling point of not exceeding 170° C., containing much amounts of water, is used repeatedly in the reaction with the bismethohalide, the increased water amounts in the reaction system cause drop of utilizing efficiency of the reactor and further fall of yield of etheramine. Furthermore, desalting is not enough, and therefore when the liquid treated with alkali metal hydroxide is subjected to crude distillation, the salts remain in the distillation pot to cause corrosion thereof.

Even if alkali metal hydroxide is added so as to be a concentration of more than 55 weight%, it brings about only economical loss due to excess addition thereof.

The operating conditions at the time of adding alkali metal hydroxide to the reaction mixture and treating it with stirring are the same as beforementioned.

Through this operation, the desalted and dehydrated liquid consisting of mainly etheramine and the aliphatic amine mixture is recovered after separated from the solid phase. The separating and recovering method can be practiced by filtration with addition of auxiliary filtration agent, decantation of the supernatant liquid, centrifugal separation or the like.

In case these recovered amines are subjected to distillation to obtain the product etheramine (boiling point 190° C./760 mmHg), the fore-running of boiling point of not exceeding 170° C. which consists of mainly the mixture of said aliphatic amine is recovered and it is reused for the reaction with the bismethohalide.

As the condition of distillation is not particularly restricted, it can be practiced under any pressure of ordinary pressure, reduced pressure or increased pressure, but it is usually practiced under ordinary pressure or reduced pressure.

In case the treated liquid undergoes distillation, only a distillate having boiling points of said aliphatic amine mixture may be recovered by rectification to be reused in the reaction with the bismethohalide, but it does not become so beneficial in the aspect of apparatus and labour.

Fundamentally, the etheramine producing process is satisfied by the simplified distillation operation comprising distillation to separate the treated liquid into a distillate of etheramine and a distillate consisting of the other composition and reusing the distillates other than etheramine for the reaction with the bismethohalide.

As mentioned above, the process of producing etheramine by this invention, wherein the aliphatic amines mixture recovered by the extremely simplified separating operation consisting of a combination of alkali metal hydroxide treatment of etheramine resulting reaction mixture with crude distillation operation can be used repeatedly as the demethylation agent, not only improves operating property remarkably but also is considered to be also a very useful method from the aspect of facilities, for it makes an industrial production of etheramine feasible by utility instruments, without any special facilities.

Furthermore, although a distillate comprising the aliphatic amines mixture recovered by the method based on this invention is used repeatedly for the reaction with the bismethohalide, etheramine can be produced at high yield.

Accordingly, this process of this invention is considered to be, from the economical aspect, a very excellent industrial methof of bis[$\beta$-(N,N-dimethylamino)ethyl]ether.

Hereinafter, this invention is explained in details by examples, but it does not undergo restrictions by these examples.

EXAMPLE 1

Preparation of bismethochloride of bis[$\beta$-(N,N-dimethylamino)ethyl]ether

Into a stainless steel autoclave of inside volume 5 liter equipped with a magnetic stirrer, 2,820 g of 30% trimethylamine aqueous solution (846 g of trimethylamine) and 860 g of bis($\beta$-chloroethyl)ether were introduced and heated at 70° C. to be subjected to a reaction for 6 hours.

After the reaction, excess of unreacted trimethylamine was purged out, and the reaction mixture was analysed. As a result of quantitative analysis of chlorine ion by Volhard method, it was 12.0 equivalents (theoretical value 12.02 equivalent).

By $^1$H-NMR and $^{13}$C-NMR analysis of the reaction mixture, it was identified that the product was bismethochloride of bis[$\beta$-(N,N-dimethylamino)ethyl]ether and it was produced nearly quantitatively.

Preparation of bis[$\beta$-(N,N-dimethylamino)ethyl]ether

Into a stainless steel autoclave of inside volume 500 ml equipped with a magnetic stirrer, 149 g of 70% bismethochloride of bis[$\mu$-(N,N-dimethylamino)ethyl]ether aqueous solution (104.3 g of bismethochloride) and 176 g of n-butylamine were introduced and heated at 170° C. for 3.5 hours to be subjected to a reaction. During the reaction, the pressure varied and the maximum pressure was about 6 kg/cm$^2$. After the reaction, the reaction mixture was added with 67 g of 48% sodium hydroxide aqueous solution and then deposited sodium chloride is filtered by the centrifugal separation. Next, as a result of quantitative analysis of the filtrate by the gas chromatography, it turned out that 51.2 g of bis[$\beta$-(N,N-dimethylamino)ethyl]ether was obtained. Based on bismethochloride, the yield thereof was 79.5%. The product was isolated by distillation and was subjected to $^1$H-NMR analysis. It was identified to be bis[$\beta$-(N,N-dimethylamino)ethyl]ether.

EXAMPLE 2

Into the same reactor as in example 1, 149 g of 70% bismethochloride of bis[$\beta$-(N,N-dimethylamino)ethyl]ether aqueous solution produced in example 1 (104.3 g of bismethochloride) and 168 g of ethylenediamine were introduced and were subjected to a reaction at 160° C. for 5 hours. As the reaction proceeded, the reaction pressure varied with lapse of time, and the maximum pressure was about 5 kg/cm$^2$.

After the reaction, the reaction mixture was added with 68 g of 48% sodium hydroxide aqueous solution and the deposited salt was filtered by the centrifugal separation. As a result of chromatographic analysis of the filtrate, it turned out that 58.6 g of bis[$\beta$-(N,N-dimethylamino)ethyl]ether was produced. Based on bismethochloride substance, the yield was 91.0%.

EXAMPLE 3-6

Into the same reactor as in example 1, 105 g of bismethochloride of bis[$\beta$-(N,N-dimethylamino)ethyl]ether and the prescribed amount of the aliphatic primary amine shown in Table 1 were introduced to be subjected to a reaction at a reaction temperature of 155°–180° C. for 2-8 hours. After the reaction, the reaction mixture was added with 70 g of 48% sodium hydroxide aqueous solution and the deposited salt was filtered by the centrifugal separation. The filtrate was analysed quantitatively by the gas chromatograph. These results were shown in Table 1.

TABLE 1

| No. of Example | aliphatic primary amine | reaction temperature (°C.) | reaction time (hour) | yield of etheramine (%) |
|---|---|---|---|---|
| 3 | butanediamine 167g | 185 | 1.0 | 91.2 |
| 4 | propanediamine 150g | 175 | 2.5 | 93.4 |
| 5 | ethylenediamine 90g | 160 | 5.0 | 90.7 |
| 6 | ethylenediamine 170g | 170 | 3.5 | 94.0 |

EXAMPLE 7

Into the same reactor as in example 1, bismethochloride of bis[β-(N,N-dimethylamino)ethyl]ether and 1,3-propanediamine were introduced in the amounts shown in Table 2 respectively to be subjected to a reaction at a reaction temperature of 170° C. and under a reaction pressure of 3.5-4.0 kg/cm$^2$ for 3.5 hours. After completion of the reaction, 48% aqueous solution of sodium hydroxide was added in amount of twice of the raw material bismethochloride substance (as NaOH). Then, water was distilled out from the reaction mixture by the distillation. After the deposited salt was removed by the centrifugal separation, the filtrate was subjected to the distillation, so a mixture of denatured compounds of 1,3-propanediamine and bis[β-(N,N-dimethylamino)ethyl]ether were separated and recovered. The recovered mixture of denatured compounds of 1,3-propanediamine was used repeatedly in the second time reaction. The same reaction and recovering operation were carried out three times. The yield of etheramine was calculated from the amount recovered by the distillation. The obtained results were shown in Table 2.

TABLE 2

| No. of Repetition | Bismethochloride (g) | 1,3-propanediamine (g) | yield of etheramine (weight %) |
|---|---|---|---|
| first time | 105 | 237 | 56.3 (87.4) |
| second time | 100 | 232* | 54.9 (88.7) |
| third time | 95 | 224* | 50.7 (86.2) |

*The demethylation agents of the second time and the third time were the mixture of denature compounds of 1,3-propanediamine (mainly N-methylated compounds) recovered after the first time reaction and the second time reaction respectively.

COMPARATIVE EXAMPLE 1

Into the same reactor as in example 1, 70 weight% aqueous solution of bismethochloride of bis[β-(N,N-dimethylamino)ethyl]ether and aminoethylethanolamine (boiling point 243.7° C.) were introduced in the amounts shown in Table 3 and were subjected to a reaction at a reaction temperature of 170° C. and under a reaction pressure of 2-3 kg/cm$^2$ for 3.5 hours. After completion of the reaction, 48% aqueous solution of sodium hydroxide was added in amount of 2.1 times of the raw material bismethochloride (as NaOH). Then, water was distilled out from the reaction mixture by the distillation. After the deposited salt was removed by the centrifugal separation, the filtrate was distilled and bis[β-(N,N-dimethylamino)ethyl]ether and the mixture of denatured compound of aminoethylethanolamine were separated and recovered. The recovered mixture of denatured compounds of aminethylethanolamine was used repeatedly in the second time reaction.

The same reaction and recovering operation were carried out three times. The yield of etheramine was calculated from the amount recovered by the distillation. The obtained results were shown in Table 3.

TABLE 3

| No. of repetition | bismethochloride (g) | aminoethylethanolamine (g) | yield of etheramine wt (g) | (%) |
|---|---|---|---|---|
| first time | 105 | 237 | 43.9 | (68.4) |
| second time | 97 | 227* | 39.2 | (66.1) |
| third time | 88 | 210* | 34.1 | (63.3) |

*The methylation agents of the second time and the third time were the mixture of denatured compounds of aminoethylethanolamine recovered after the first time reaction and the second time reaction respectively.

EXAMPLE 8

Into a stainless steel autoclave of inside volume 5 liter equipped with a magnetic sitrrer, 1,258 g of 70% aqueous solution of bismethochloride of bis[β-(N,N-dimethylamino)ethyl]ether, (880.6 g of bismethochloride) and 1,800 g of ethylenediamine were introduced and were subjected to a reaction at a reaction temperature of 150° C. and at a pressure of 2.8-3.5 kg/cm$^2$ for 6 hours. After completion of the reaction, the reaction mixture was cooled to the room temperature and was transferred to a separating funnel of inside volume 5 liter.

The reaction mixture separated uniformly into two layers of upper and lower ones was taken out respectively to recover 730 g of the upper layer liquid and 2,317 g of the lower layer liquid.

As a result of chromatographic analysis of the upper layer liquid, it was recognized that 469 g of etheramine was present. The recovered upper layer liquid was distilled to be separated into a low boiling temperature mixture having the boiling point of not exceeding 140° C. and etheramine (boiling point being about 190° C.). The lower layer liquid was transferred to a four neck flask made of gloss equipped with a stirrer and a refluxing cooler and was added with 620 g of solid hydroxide. They were treated with stirring at a temperature of 80°-90° C. for 4 hours. From the mixture treated with sodium hydroxide, 1,820 g of supernatant liquid was recovered. As a result of gas-chromatographic analysis of the supernatant liquid, it was asertained that 19.8 g of etheramine and 1,630 g of ethylene diamine and N-methylated ethylenediamines (the denatured compounds of ethylenediamine) were present.

The total amount 2,070 g of the low boiling point mixture of 250 g recovered from the upper layer liquid and the supernatant liquid 1,820 g recovered from the lower layer liquid was mentioned above were used as the demethylation agent for the second time production of etheramine. With performance of the same recovering procedures, the repeated reactions were carried out four times in the same conditions as in the first time reaction.

The yield of etheramine was calculated by substracting the amount of etheramine introduced into the reaction system with the denatured compounds mixture of ethylenediamine from the amount of the produced etheramine in the reaction mixture. Ethylenediamine recovered from the upper layer and lower layer was without any fresh ethylenediamine additional supply, used repeatedly. The result was shown in Table 4.

TABLE 4

| No. of repetition | 70% aqueous solution of bismetho-chloride (g) | solid NaOH addition amount (g) | NaOH concentration (wt %) | etheramine (g) | yield (%) |
| --- | --- | --- | --- | --- | --- |
| 1st time | 1258 | 620 | 42.8 | 488.8 | 90.0 |
| 2nd time | 1258 | 820 | 46.3 | 489.3 | 90.1 |
| 3rd time | 1258 | 820 | 46.5 | 487.0 | 89.7 |
| 4th time | 1258 | 500 | 26.7 | 475.2 | 87.5 |

EXAMPLE 9

Into the same reactor as in example 8, 85% aqueous solution 921.7 g of bismethochloride of bis[β-(N,N-dimethylamino)ethyl]ether (783.7 g of bismethochloride) and 1,550 g of 1,3-propanediamine were introduced and were subjected to a reaction at a reaction temperature 170° C. and a reaction pressure 3.5–4.5 kg/cm² for 4 hours. After completion of the reaction, the reaction mixture was cooled to the room temperature and was transferred to a separating funnel.

The reaction mixture separated into two layers of upper and lower ones was taken out respectively to recover 660 g of the upper layer liquid and 1,794 g of the lower layer liquid. As a result of gas-chromatographic analysis of the upper layer liquid, the existance of etheramine 427 g was recognized, the lower layer liquid was transferred to a four neck flask made of glass equipped with a stirrer and a refluxing cooler and was added with 351 g of solid sodium hydroxide. They were treated with stirring at a temperature of 60°–80° C. for 5 hours.

After this treated liquid was left to stand, 1,460 g of a supernatant liquid was recovered. As a result of gas-chromatographic analysis of the supernatant liquid, it was recognized that 18 g of etheramine and 1,370 g of 1,3-propanediamine and N-methylated compounds mixture were present. In the second time reaction of producing etheramine, 1,510 g of the supernatant liquid containing 1,370 g of the denatured compounds mixture of 1,3-propanediamine recovered from the lower layer liquid was, with an additional supply of 1,3-propanediamine 200 g, used as the demethylation agent.

In the repeated reaction, the same separating and recovering procedures were also carried out at the second and the further following times, and the obtained treated liquid of the lower layer additionally supplemented with 200 g of fresh 1,3-propanediamine was used as the demethylation agent in the next time reaction.

The recovery and reusing of the denatured compounds mixture of 1,3-propanediamine from the upper layer after the reaction of producing etheramine were not carried out.

The yield of etheramine was calculated in the same way as in example 8. The repeated reactions were carried out four times and these results were shown in Table 5.

TABLE 5

| No. of repetition | the raw material bismetho-chloride (g) | addition amount of 1,3-propane-diamine (g) | addition amount of solid NaOH (g) | NaOH concentration (wt %) | etheramine (g) | yield (%) |
| --- | --- | --- | --- | --- | --- | --- |
| 1st time | 921.7 | 1550 | 351 | 31.7 | 445 | 92 |
| 2nd time | 921.7 | 200 | 350 | 40.5 | 438 | 90.6 |
| 3rd time | 921.7 | 200 | 340 | 40.6 | 430 | 89.0 |
| 4th time | 921.7 | 200 | 300 | 30.6 | 426 | 88.0 |

COMPARATIVE EXAMPLE 2

Into the same reactor as in example 8, 70% aqueous solution 746.3 g of bismethochloride of bis[β-(N,N-dimethylamino)ethyl]ether (522.4 g of bismethochloride) and 1,080 g of ethylenediamine were introduced and were subjected to a reaction at a reaction temperature 160° C. and under a reaction pressure 3.5–4.5 kg/cm² for 6 hours. After completion of the reaction, the reaction mixture was cooled to the room temperature and was transferred to a separating funnel. The reaction mixture separated into two layers of upper and lower ones was taken out separately to recover 435 g of the upper layer liquid and 1,375 g of the lower layer liquid. As a result of gas-chromatographic analysis of the upper layer, the existance of etheramine 277.7 g was recognized. The recovered upper layer liquid was separated by distillation to recover 155 g of low boiling point mixture having boiling points of not exceeding 140° C. and etheramine. The lower layer liquid was transferred to a four neck flask made of glass equipped with a stirrer and a refluxing cooler and was added with 179 g of solid sodium hydroxide. They were treated with stirring at a temperature of 60°–90° C. for 4 hours.

After leaving to stand, 1,245 g of supernatant liquid was recovered. As a result of gas-chromatographic analysis of this supernatant liquid, it was recognized that 11.6 g of etheramine and 997 g of a mixture of ethylendiamine with a mixture of N-methylated denatured compounds thereof were present.

The total amount 1,400 g of the low boiling mixture (155 g) having boiling point of not exceeding 140° C. recovered from the upper layer liquid and the supernatant liquid (1,245 g) recovered from the lower layer as mentioned above was used as the demethylation agent in the second time reaction of producing etheramine.

To the upper layer liquid and lower layer liquid after the reaction of producing etheramine, the same separating and recovering procedures were applied and the repeated reactions were carried out three times, employing the demethylation agent recovered from the reaction mixture of two layers of the upper and lower ones.

The yield of etheramine was calculated in the same way as in example 8. The results of the repeated reaction were shown in Table 6.

TABLE 6

| No. of repetition | 70% aqueous solution of bismetho-chloride (g) | addition amount of solid NaOH (g) | NaOH concentration (wt %) | etheramine (g) | yield (%) |
| --- | --- | --- | --- | --- | --- |
| 1st time | 746.3 | 179 | 6.4 | 289.3 | 89.8 |
| 2nd time | 746.3 | 190 | 5.4 | 272.9 | 84.7 |
| 3rd time | 746.3 | 190 | 3.7 | 246.5 | 76.5 |

EXAMPLE 10

Into the same reactor as in example 8, 1,258 g of 70% aqueous solution of bismethochloride of bis[β-(N,N-dimethylamino)ethyl]ether (880.6 g of bismethochloride) and 1,416 g of ethylenediamine were introduced and were subjected to a reaction at a reaction temperature 155° C. and under a reaction pressure 2.5-3.5 kg/cm² for 5 hours. The reaction mixture was taken out after cooled and was transferred to a four neck flask made of glass equipped with a stirrer, an inserting pipe of the thermometer and a refluxing cooler. Then, it was added with 694 g of solid sodium hydroxide and treated with stirring at a temperature of 50°-60° C. for 2.5 hours. From the solid phase sedimented toward the lower layer, 2,150 g of a supernatant liquid was separated and recovered, and it was transferred to a distillation pot.

With use of a column for distillation whose column height was 50 cm (filled with Raschig rings made of glass), the supernatant recovered liquid was subjected to a distillation under ordinary pressure to give 1,655 g of a distillate of column head temperature 90°-125° C. (fraction-I).

As a result of practicing gas-chromatographic analysis thereof, it was ascertained that, 1,480 g of ethylenediamine and N-methylated ethylenediamines (the denatured compounds of ethylenediamine) was present.

Subsequently, it was subjected to the reduced pressure distillation to give 456 g of a distillate of column head temperature 132° C. (165 mmHg) (fraction-II).

As a result of gas-chromatographic analysis thereof, it could be ascertained that the fraction-II was bis[β-(N,N-dimethylamino)ethyl]ether. The distillate of the fraction-I 1,655 g was used as such in the second time reaction for producing etheramine. Performing the same separating and recovering procedures, the repeated reactions were carried out three times under the same condition. Without any additional supplement of ethylenediamine, only the recovered mixture of denatured compounds of ethylenediamine was used repeatedly. The results were shown in Table 7.

TABLE 7

| No. of repetition | 70% aqueous solution of bismethochloride (g) | addition amount of solid NaOH (g) | NaOH concentration (wt %) | etheramine (g) | yield (%) |
|---|---|---|---|---|---|
| 1st time | 1258 | 694 | 46.0 | 456 | 84.0 |
| 2nd time | 1258 | 824 | 47.3 | 451 | 83.1 |
| 3rd time | 1258 | 820 | 47.1 | 444 | 81.8 |

EXAMPLE 11

Into the same reactor as in example 8, 1,300 g of 73% aqueous solution of bismethochloride of bis[β-(N,N-dimethylamino)ethyl]ether (949 g of bismethochloride) and 1,884 g of 1,3-propanediamine were introduced and were subjected to a reaction at a reaction temperature 150° C. and under a reaction pressure 2-3 kg/cm² for 7 hours. After the reaction, the reaction mixture was cooled and was added with 620 g of solid sodium hydroxide through the opened cover of the reactor. After cover was closed again, it was heated with stirring at 70°-90° C. for 2 hours. Then, 2,710 g of a supernatant liquid was separated and recovered from the solid phase of the lower layer. Employing the same column for distillation as in example 10, the supernatant recovered liquid was subjected to a distillation under ordinary pressure to give 2,108 g of a distillate of column head temperature 90°-180° C. (fraction-I).

As a result of practicing gas-chromatographic analysis thereof, it was recognized that 1,920 g of propanediamine and N-methylated propanediamines (the denatured compounds of propanediamine) was present. Subsequently, it was subjected to the reduced pressure distillation to give 513 g of a distillate of column head temperature 132° C. (160 mmHg) fraction-II).

As a result of gas-chromatographic analysis thereof, there could be ascertained 509 g of bis[β-(N,N-dimethylamino)ethyl]ether in the fraction-II.

The distillate of the fraction-I 2,108 g was used as such in the second time reaction for producing etheramine. Performing the same separating and recovering procedures, the repeated reactions were carried out four times. Without any additional supplement of propanediamine, only the recovered mixture of denatured compounds of propanediamine was used repeatedly. The results were shown in Table 8.

TABLE 8

| No. of repetition | 70% aqueous solution of bismethochloride (g) | addition amount of solid NaOH (g) | NaOH concentration (wt %) | etheramine (g) | yield (%) |
|---|---|---|---|---|---|
| 1st time | 1300 | 620 | 40.6 | 509 | 87.0 |
| 2nd time | 1300 | 690 | 37.0 | 496 | 84.9 |
| 3rd time | 1300 | 730 | 38.6 | 486 | 83.1 |
| 4th time | 1300 | 710 | 35.0 | 476 | 81.4 |

COMPARATIVE EXAMPLE 3

Into the same reactor as in example 8, 1,000 g of 70% aqueous solution of bismethochloride of bis[β-(N,N-dimethylamino)ethyl]ether (700 g of bismethochloride) and 1,300 g of ethylenediamine were introduced and were subjected to a reaction at a reaction temperature 150° C. and under a reaction pressure 2.5-3.5 kg/cm² for 7 hours.

After the reaction, 249 g of solid sodium hydroxide was added to the reaction mixture by the same procedure as in example 10, and it was heated with stirring at 70°-80° C. for 3 hours. After leaving it to stand, 2,173 g of a supernatant liquid was separated and recovered from the solid phase of the lower layer. Employing the same column for distillation as in example 10, the supernatant recovered liquid was subjected to a distillation under ordinary pressure to give 1,785 g of a distillate of column head temperature 90°-127° C. (fraction-I).

As a result of gas-chromatographic analysis thereof, there could be ascertained 363 g of bis[β-(N,N-dimethylamino)ethyl]ether in the fraction-II.

The distillate of fraction-I, 1,785 g was used as such in the second time reaction for producing etheramine. The repeated reactions were likewise carried out three times. The results were shown in Table 9.

TABLE 9

| No. of repetition | 70% aqueous solution of bismethochloride (g) | addition amount of solid NaOH (g) | NaOH concentration (wt %) | etheramine (g) | yield (%) |
|---|---|---|---|---|---|
| 1st time | 1000 | 249 | 8.1 | 363 | 84.1 |
| 2nd time | 1000 | 280 | 8.0 | 333 | 77.2 |
| 3rd time | 1000 | 309 | 8.0 | 310 | 71.9 |

What is claimed is:

1. A method for producing bis[β-(N,N-dimethylamino)alkyl]ether by reacting a bismethohalide of a bis[β-(N,N-dimethylamino)alkyl]ether represented by the following general formula

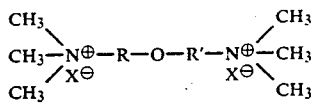

wherein R and R' denote alkyl groups having 2-3 carbon atoms and X denotes halogen atom, with an aliphatic amine having a boiling point of 40°-170° C. at atmospheric pressure and having one or two primary amine groups in the molecule thereof under an increased pressure.

2. The method for producing bis[β-(N,N-dimethylamino)alkyl]ether recited in claim 1, wherein the bismethohalide is the bismethochloride of bis[β-(N,N-dimethylamino)ethyl]ether.

3. The method for producing bis[β-(N,N-dimethylamino)alkyl]ether recited in claim 1, the aliphatic amine is butylamine, ethylenediamine, propanediamine or butanediamine.

4. The method for producing bis[β-(N,N-dimethylamino)alkyl]ether recited in claim 1, wherein the aliphatic amine is added by at least 2 mol to 1 mol of the bismethohalide.

5. The method for producing bis[β-(N,N-dimethylamino)alkyl]ether recited in claim 1, wherein the reaction of the bismethohalide with the aliphatic amine is carried out at a temperature of 140°-190° C.

6. The method for producing bis[β-(N,N-dimethylamino)alkyl]ether recited in claim 1, wherein the aliphatic amine is recovered from the reaction mixture and is reused in the repeated reaction.

7. The method for producing bis[β-(N,N-dimethylamino)alkyl]ether recited in claim 6, wherein the aliphatic amine is recovered by adding alkali compound to the reaction mixture, followed by neutralization and separation means.

8. A method for producing bis[β-(N,N-dimethylamino)ethyl]ether wherein a bismethohalide compound of bis[β-(N,N-dimethylamino)ethyl]ether represented by a general formula

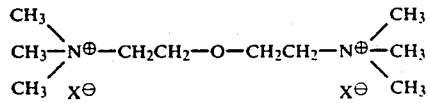

(X denotes halogen atom)

is reacted with an aliphatic amine, which is characterized by comprising the following steps (a) (b) (c):

(a) step of separating and recovering an upper layer liquid and a lower layer liquid respectively from a reaction mixture having two separated upper and lower layers obtained by the reaction of said bismethohalide compound with the aliphatic amine having primary or secondary amino group (b) step of adding alkali metal hydroxide to the lower layer liquid so as to be in a concentration of 10-55 weight% to water amount of the lower layer liquid, followed by recovering the aliphatic amine (c) step of further reusing the recovered aliphatic amine for the repeated reaction with said bismethohalide compound.

9. The method for producing bis[β-(N,N-dimethylamino)ethyl]ether recited in claim 8, wherein the aliphatic amine has a boiling point of 40°-170° C. under an atmospheric pressure and has one or two primary amino group in the molecule thereof.

10. The method for producing bis[β-(N,N-dimethylamino)ethyl]ether recited in claim 8, wherein the aliphatic amine is propylamine, butylamine, ethylenediamine, propanediamine or butanediamine.

11. The method of producing bis[β-(N,N-dimethylamino)ethyl]ether recited in claim 8, wherein alkali metal hydroxide is sodium hydroxide and/or potassium hydroxide.

12. A method for producing bis[β-(N,N-dimethylamino)ethyl]ether wherein bismethohalide compound of bis[β-(N,N-dimethylamino)ethyl]ether represented by a general formula

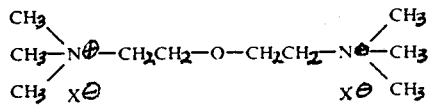

(X denotes halogen atom)

is reacted with an aliphatic amine having boiling point of 40°-170° C. under atmospheric pressure and having 1-2 primary amino group in the molecule thereof, which is characterized by comprising the following steps (a) (b) (c) (d):

(a) step of adding alkali metal hydroxide so as to be 10-55 weight% to water amount in the reaction system, after completion of the reaction of said bismethohalide compound with said aliphatic amine (b) step of separating and recovering a liquid phase consisted of the amine (c) step of separating by distillation of the recovered amine into a distillate of boiling point of not exceeding 170° C. and a distillate of that of exceeding 170° C.

(d) step of reusing the recovered amine having boiling point of not exceeding 170° C. under atmospheric pressure in the repeated reaction with said bismethohalide.

13. The method for producing bis[β-(N,N-dimethylamino)ethyl]ether recited in claim 12, wherein the aliphatic amine is propylamine, butylamine, ethylenediamine, propanediamine or butenediamine.

14. The method for producing bis[β-(N,N-dimethylamino)ethyl]ether recited in claim 12, wherein alkali metal hydroxide is sodium hydroxide and/or potassium hydroxide.

* * * * *